United States Patent [19]

Reimels

[11] Patent Number: 5,580,347
[45] Date of Patent: Dec. 3, 1996

[54] CONTROLLING OPERATION OF HANDPIECES DURING OPHTHALMIC SURGERY

[75] Inventor: Harry G. Reimels, Braintree, Mass.

[73] Assignee: Mentor Ophthalmics, Inc., Norwell, Mass.

[21] Appl. No.: 307,027

[22] Filed: Sep. 15, 1994

Related U.S. Application Data

[63] Continuation of Ser. No. 73,968, Jun. 8, 1993, abandoned, which is a continuation of Ser. No. 738,594, Jul. 31, 1991, abandoned.

[51] Int. Cl.$^6$ .......................... A61M 1/00; A61M 31/00; A61B 17/20
[52] U.S. Cl. .............. 604/30; 604/22; 604/27; 604/35; 604/51
[58] Field of Search ............ 128/24 AA, 750–752, 128/755, 758, 760, 763, 765–766; 601/2, 6, 9, 10, 13; 604/22, 27, 30, 31, 35, 51, 902; 606/169–171

[56] References Cited

U.S. PATENT DOCUMENTS

| | | |
|---|---|---|
| 3,659,607 | 5/1972 | Banko . |
| 3,693,613 | 9/1972 | Kelman . |
| 3,732,858 | 5/1973 | Banko . |
| 3,901,231 | 8/1975 | Olson ................................. 128/D12 |
| 4,016,882 | 4/1977 | Broadwin et al. .................... 606/169 |
| 4,168,707 | 9/1979 | Douvas et al. ....................... 128/D13 |
| 4,190,059 | 2/1980 | Holt .................................... 604/27 |
| 4,315,520 | 2/1982 | Atkinson et al. ..................... 137/82 |
| 4,428,748 | 1/1984 | Peyman et al. ...................... 606/171 |
| 4,517,963 | 5/1985 | Michel . |
| 4,705,500 | 11/1987 | Reimels et al. ...................... 604/35 |
| 4,757,814 | 7/1988 | Wang et al. . |
| 4,764,165 | 8/1988 | Reimels et al. ...................... 604/35 |
| 4,817,599 | 4/1989 | Drews ................................. 606/107 |
| 5,026,387 | 6/1991 | Thomas ............................. 128/24 AA |
| 5,053,002 | 10/1991 | Barlow ................................ 604/30 |
| 5,157,603 | 10/1992 | Scheller et al. ...................... 604/22 |
| 5,188,102 | 2/1993 | Idemoto et al. .................... 128/24 AA |
| 5,209,719 | 5/1993 | Baruch et al. ..................... 128/24 AA |
| 5,211,625 | 5/1993 | Sakurai et al. .................... 128/24 AA |
| 5,242,404 | 9/1993 | Conley et al. ........................ 604/30 |

FOREIGN PATENT DOCUMENTS

| | | |
|---|---|---|
| 0095926 | 7/1983 | European Pat. Off. . |
| 3539955 | 5/1987 | Germany . |
| 2132893 | 7/1984 | United Kingdom . |

OTHER PUBLICATIONS

Alcon® Surgical, Inc., "Series Ten Thousand Master Cataract System" advertisement, Fort Worth, Texas, 1989, two pages.

Dutch Ophthalmic Research Center by, "Harmony Micro Surgical System for Anterior and Posterior Segment Surgery" brochure, Holland, Nov., 1990, eight pages.

(List continued on next page.)

*Primary Examiner*—Randall L. Green
*Assistant Examiner*—P. Zuttarelli
*Attorney, Agent, or Firm*—Fish & Richardson P.C.

[57] ABSTRACT

A system for performing surgery on a patient's eye includes a handpiece constructed for insertion into the eye, a control module, and a foot pedal module. The control module includes at least one control arranged for setting at least one parameter of operation of the handpiece (e.g., aspiration rate, intensity of phaco-power, etc.). The foot pedal module includes a foot pedal with which operation of the handpiece is controllable in accordance with the parameter set by the control in the control module. For example, the foot pedal may be used to vary the aspiration rate or the intensity of phaco-power up to the maximum set by a control on the control module. The foot pedal module includes circuitry for controlling operation of the handpiece in response to depression of the foot pedal and in accordance with the parameter set by the control in the control module. That is, processing circuitry is located in the foot pedal module rather than the control module, which enables the control module to be relatively compact.

20 Claims, 10 Drawing Sheets

OTHER PUBLICATIONS

Staar® Surgical Company, "Phaco XL™ Instrument" advertisement, Monrovia, California, Feb., 1991, one page.

Allergan Medical Optics, "Man and His Machines. The Perfect Partnership" PhacoPlus® brochure, Irvine, CA, 1990, seven pages.

United Surgical, "Incisions that Start Small Should Stay Small" PhacoMates™ brochure, Irvine, California, 1989, four pages.

Site Microsurgical, "Site TXR® Is Your Total Surgical Phaco System" advertisement, Horsham, Pennsylvania, Nov., 1990, four pages.

Surgical Design Corporation, "Surgical Design Ocusystem II" brochure, New York, Nov., 1990, four pages.

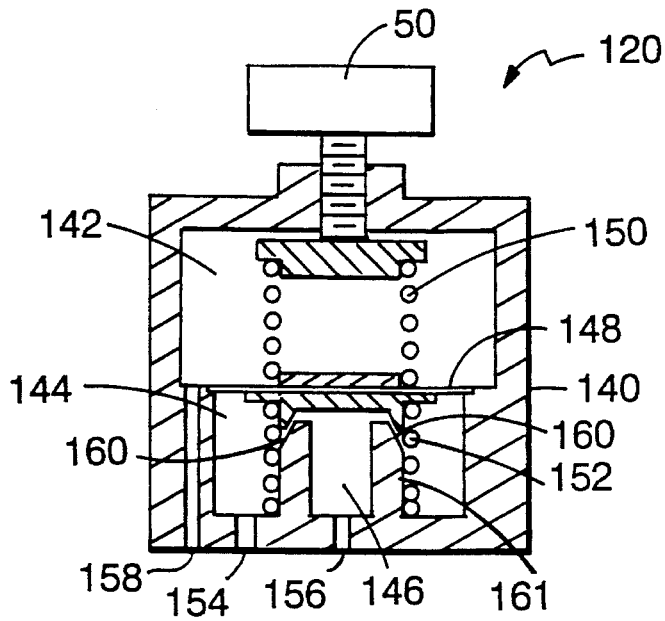
FIG. 12
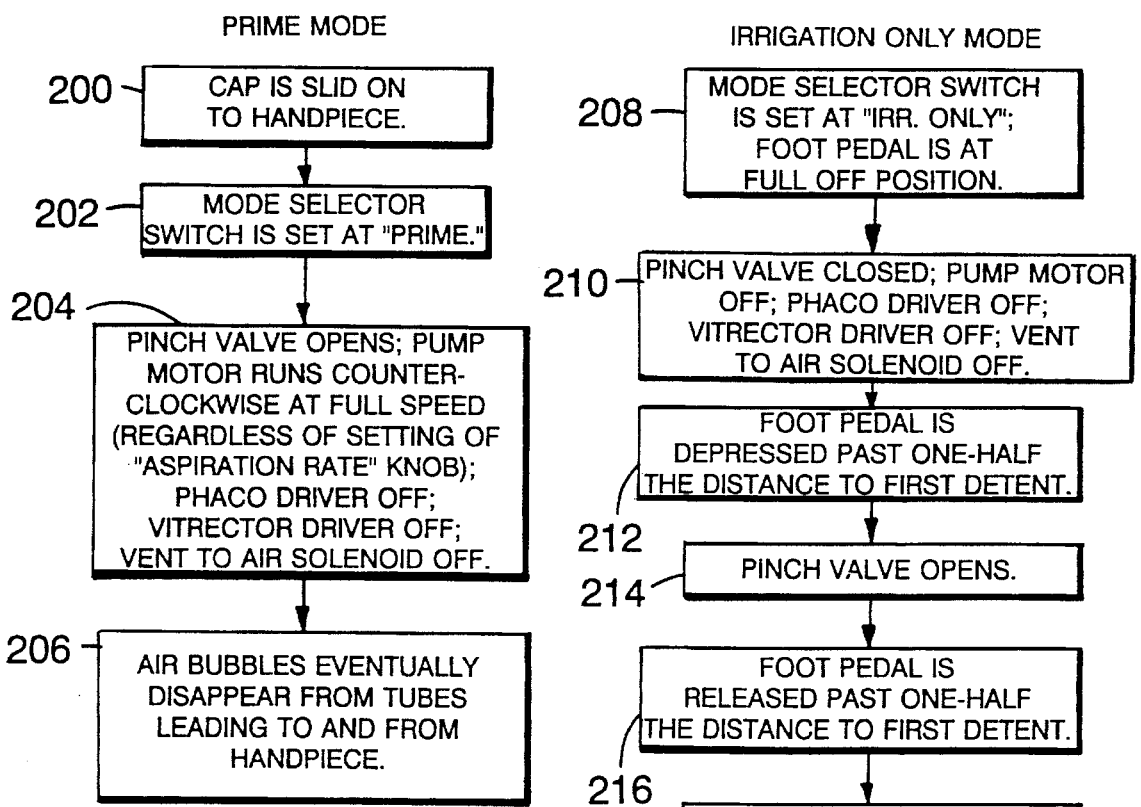

CONTROLLING OPERATION OF HANDPIECES DURING OPHTHALMIC SURGERY

This is a continuation of application Ser. No. 08/073,968, filed Jun. 8, 1993, now abandoned, which was a continuation of application Ser. No. 07/738,594, filed Jul. 31, 1991, now abandoned.

BACKGROUND OF THE INVENTION

The present invention relates in general to devices and methods for controlling the operation of handpieces during ophthalmic surgery and more particularly concerns control of irrigation, aspiration, phaco-emulsification, and vitrector cutting during surgery to remove cataracts.

During cataract surgery it is necessary to remove an opaque lens from the patient's eye. One method of removing the lens is known as phaco-emulsification. First, a small incision is made on the side of the cornea and the lens membrane is punctured. Then, the lens is ultrasonically shattered using a phaco-emulsification instrument that irrigates the eye and aspirates particles of the lens as the lens is being emulsified. A silicone replacement lens is then folded and fed through the small corneal incision. Alternatively, the opening is enlarged to a size sufficient to permit insertion of a conventional hard lens.

The handpiece used during the incision of the cornea and puncturing of the lens membrane and the handpiece used during phaco-emulsification are typically controlled by a control module in conjunction with a foot pedal module. The foot pedal module provides linear control over the aspiration rate, the intensity of power applied to the phaco handpiece, etc. within parameters (e.g., maxima and minima) selected by a variety of control knobs or buttons on the control module. The control module includes a variety of displays for displaying the aspiration rate, vacuum pressure during aspiration, power applied to the phaco handpiece, etc. The control module also includes circuitry, responsive to the control knobs or buttons on the control module and responsive to the foot pedal module, for controlling an aspiration pump, vacuum pressure regulator, phaco-power driver, etc. and for controlling the displays on the control module.

SUMMARY OF THE INVENTION

According to one aspect of the invention, a system for performing surgery on a patient's eye includes a handpiece constructed for insertion into the eye, a control module, and a foot pedal module. The control module includes at least one control arranged for setting at least one parameter of operation of the handpiece (e.g., aspiration rate, intensity of phaco-power, etc.). The foot pedal module includes a foot pedal with which operation of the handpiece is controllable in accordance with the parameter set by the control in the control module. For example, the foot pedal may be used to vary the aspiration rate or the intensity of phaco-power up to the maximum set by a control on the control module. The foot pedal module includes circuitry for controlling operation of the handpiece in response to depression of the foot pedal and in accordance with the parameter set by the control in the control module.

That is, processing circuitry is located in the foot pedal module rather than the control module, which enables the control module to be relatively compact. As a result, the control module can be located close to the patient, e.g. on a stand with an IV bottle and a refuse pouch, without physically interfering with the surgeon's work. Thus, the control module is readily accessible to the surgeon or a scrub nurse in the immediate vicinity of the patient. One of the advantages of having the control module close to the patient is that a relatively small pump can be used for aspiration because the aspiration tube connecting the aspiration pump to the handpiece can be made relatively short. Small pumps are easily reversible in their direction of operation and can operate in a "reflux" mode to eject particles that become lodged in the aspiration tube or the handpiece.

According to another aspect of the invention, the control module includes a plurality of controls each of which is arranged to be adjusted to multiple positions by the user for varying a respective parameter of operation of the handpiece (e.g., aspiration rate, intensity of phaco-power, etc.). The adjusted positions of the plurality of controls provide exclusive visual feedback with respect to the parameters of operation of the handpiece (e.g., no digital displays, readouts, etc.).

The control module is therefore relatively simple to use and inexpensive. More importantly, the surgeon is free to concentrate on the surgery itself rather than visually monitoring the displays on the control module. By eliminating separate visual feedback devices the invention accommodates the many surgeons who do not look at visual feedback displays at all during opthalmic surgery. The simple design according to the invention enables the surgeon simply to instruct a scrub nurse to manipulate a control on the control module to switch from one mode of operation to another during surgery.

According to another aspect of the invention, a pump is connected to the handpiece by tubing, the pump being arranged to produce aspiration through the tubing. The control module is connected to the tubing and includes a vacuum regulator arranged for controlling pressure within the tubing. Visual feedback is provided solely through observation of the physical location of the vacuum regulator. For example, the vacuum regulator is controlled by a knob that sweeps through the entire available range of vacuum pressures within one rotation, thereby eliminating the need for separate visual feedback devices and providing ease of use.

According to another aspect of the invention, the pump is arranged to operate in a first direction to produce aspiration through the handpiece and the tubing, and a reflux switch is arranged to override operation of the foot pedal regardless of the position of the foot pedal by causing the pump to operate in a second direction opposite to the first direction to force fluid through the tubing in a direction opposite to the direction in which fluid flows through the tubing during aspiration. The reflux switch provides a convenient way for the surgeon to enter a "reflux" mode of operation without requiring the surgeon to manipulate the controls on the control module (an overall goal of the various aspects of the invention being to reduce the need for the surgeon to interact with the control module).

According to another aspect of the invention, the foot pedal in the foot pedal module controls application of electrical power to the handpiece (e.g., controls the application of phaco-power to a phaco-emulsification handpiece). An auditory indicator (e.g., a beeper) produces sounds indicating an amount of time during which the electrical power has been applied to the handpiece (e.g., one beep after 30 seconds, two beeps after a minute, etc.). By providing an auditory indication, the need for visual feedback and observation of a timer is eliminated.

According to another aspect of the invention, the aspiration pump operates in a first direction to produce aspiration through the handpiece and the tubing and operates in a second direction in a reflux mode to force fluid through the tubing in a direction opposite to the direction in which fluid flows through the tubing during aspiration. An auditory indicator (e.g., a beeper) produces an audible signal while the pump is operating in the reflux mode. Again, the auditory indication eliminates the need for visual feedback and observation.

Numerous other features, objects, and advantages of the invention will become apparent from the following detailed description, and from the claims.

DETAILED DESCRIPTION

We first briefly describe the drawings.

Drawings

FIG. 12 is a cross-sectional view of a vacuum regulator used in the control module of FIG. 2.

FIG. 13 is a flowchart illustrating the operation of the ophthalmic surgery system of FIG. 1 during the "prime" mode.

FIG. 14 is a flowchart illustrating the operation of the ophthalmic surgery system of FIG. 1 during the "irrigation only" mode.

Structure

Figure 1:
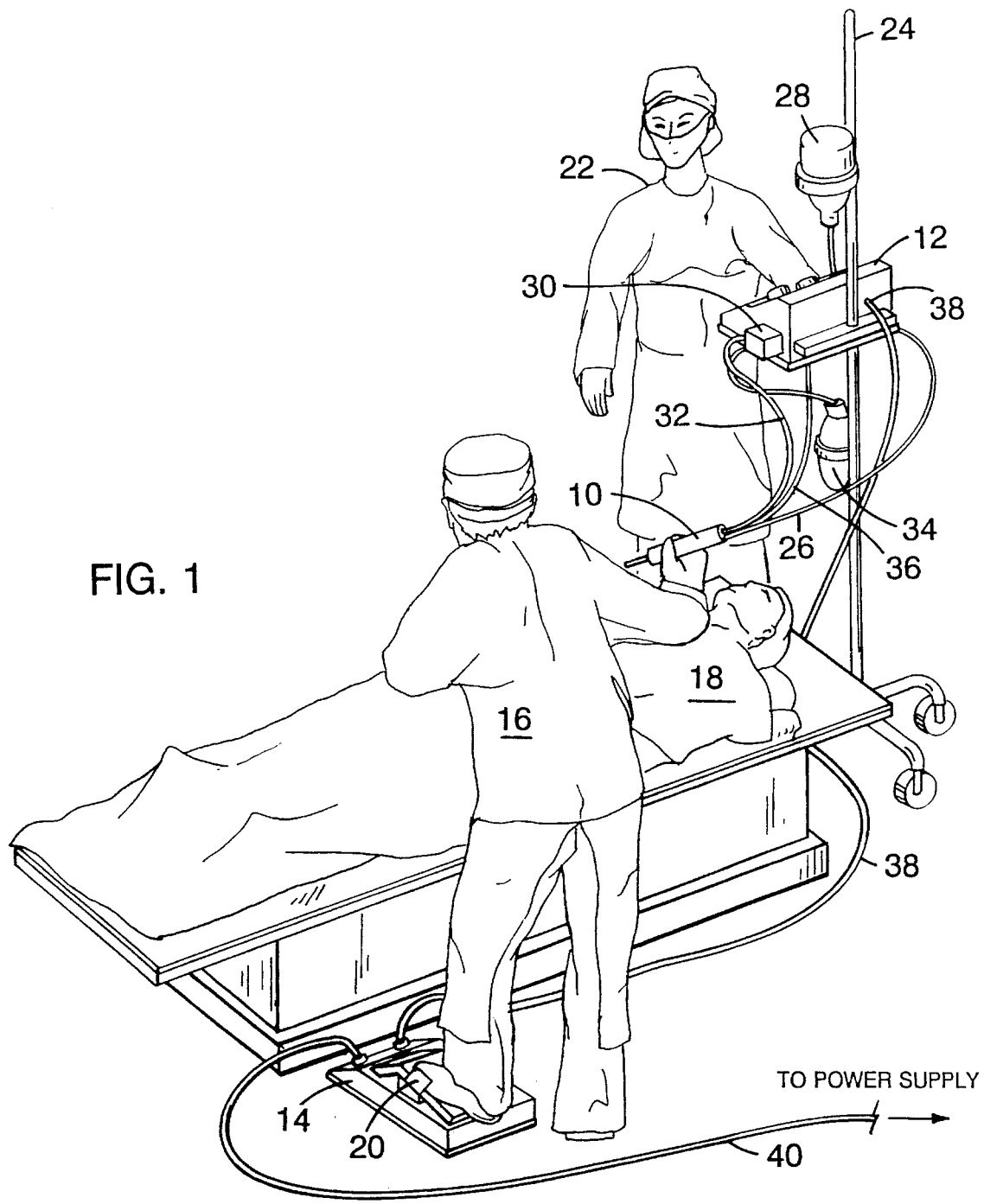
FIG. 1 shows an ophthalmic surgery system in accordance with the invention.
Figure 2:
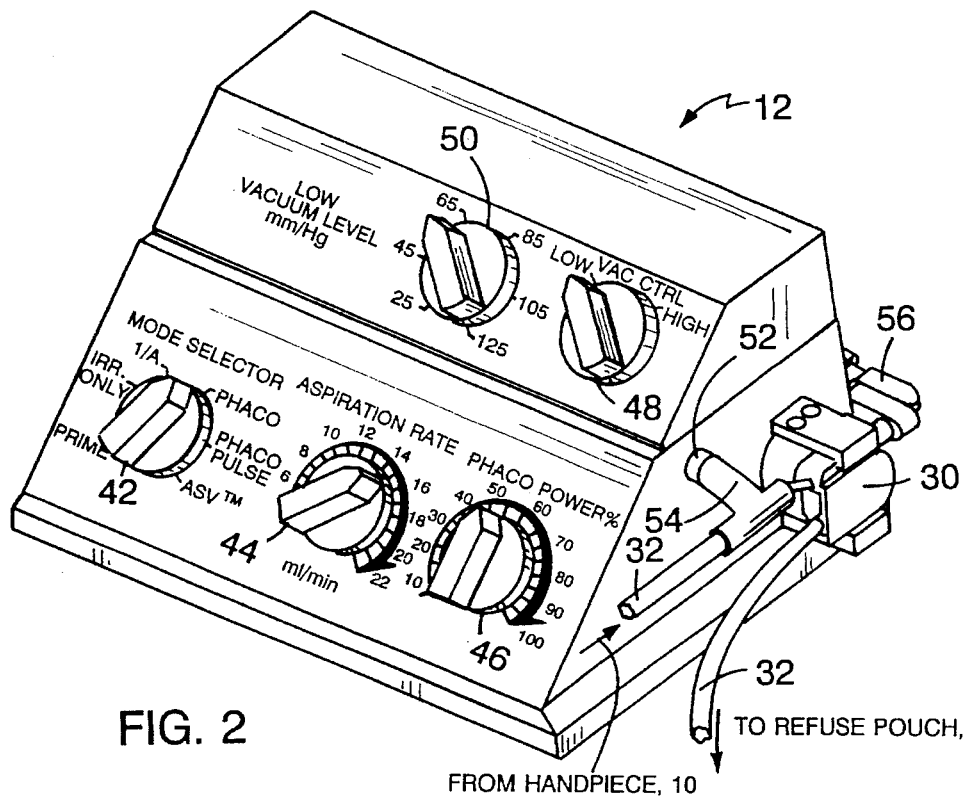
FIG. 2 is an isometric drawing of the control module shown in FIG. 1.
Figure 3:
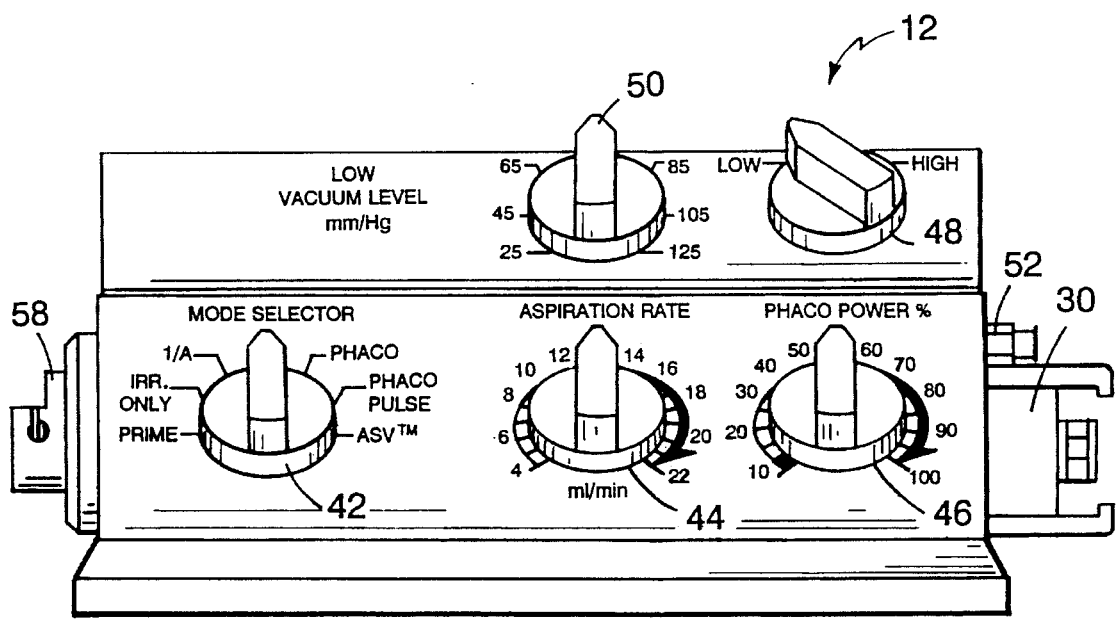
FIG. 3 is a front view of the control module of FIG. 2.
Figure 4:
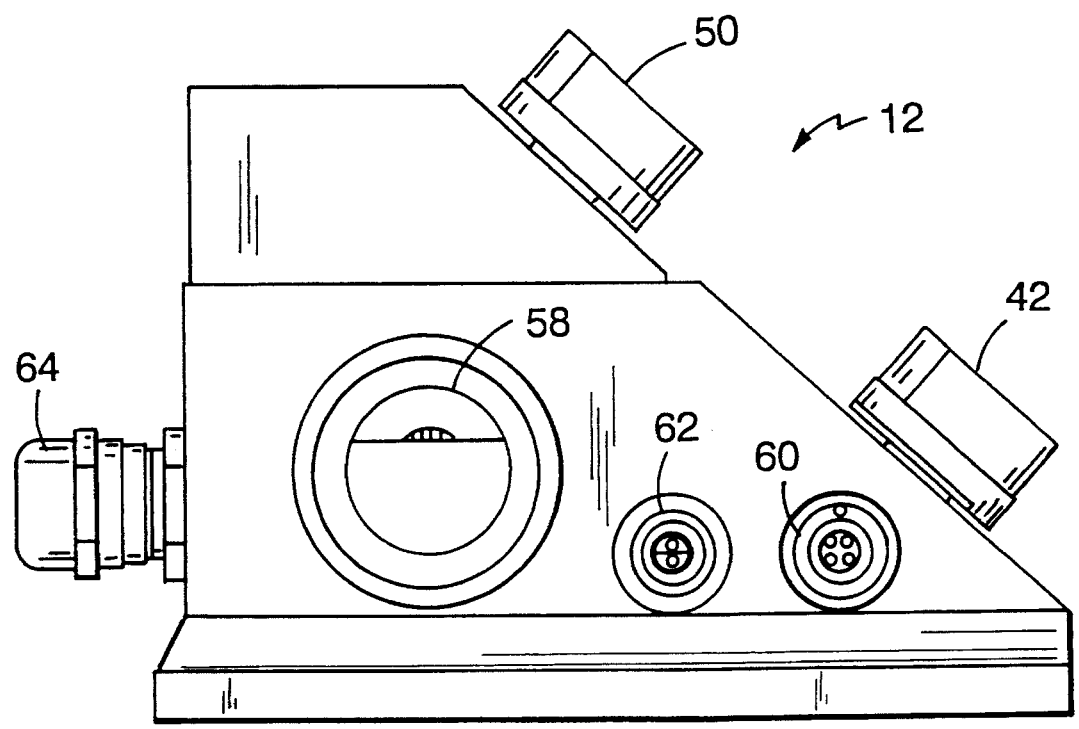
FIG. 4 is a side view of the control module of FIG. 2 as seen from the left side.
Figure 5:
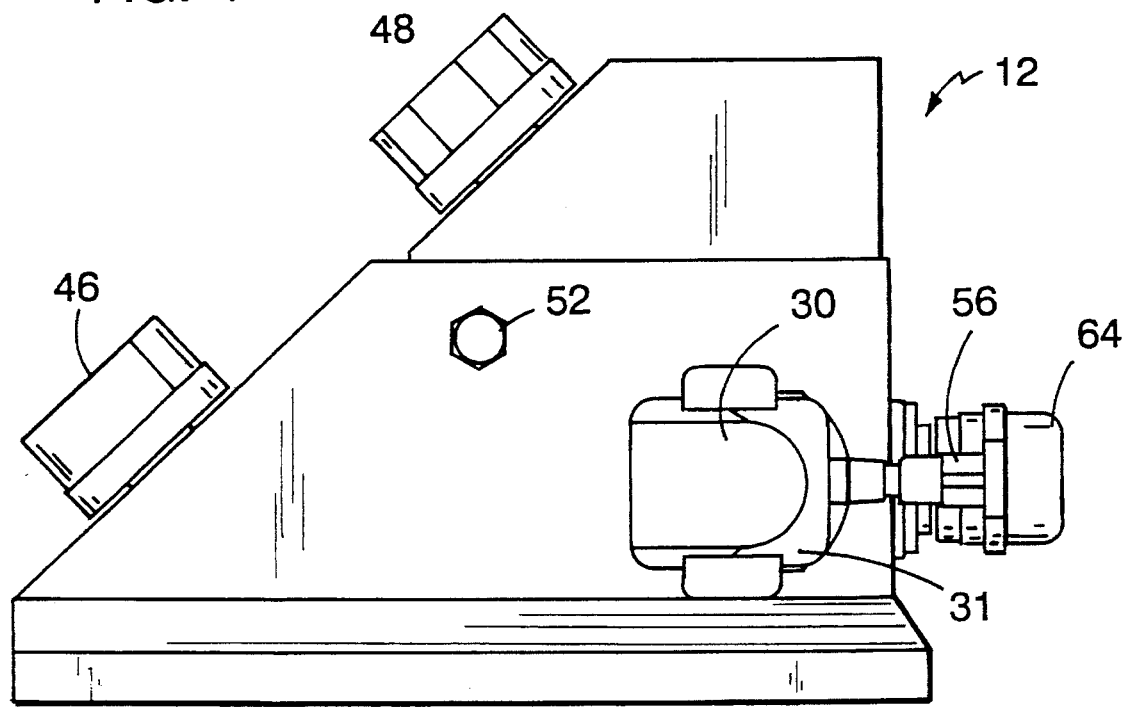
FIG. 5 is a side view of the control module of FIG. 2 as seen from the right side.

With reference now to the drawings and more particularly FIG. 1 thereof, an opthalmic surgery system includes handpiece 10, compact control module 12, and foot pedal module 14. Surgeon 16 operates on the eye of a patient 18 while controlling the operation of handpiece 10 by depressing foot pedal 20 of foot pedal module 14, while a scrub nurse 22 adjusts the controls of control module 12, which is mounted on stand 24. (Alternatively stand 24 is positioned adjacent to the surgeon, and the surgeon sets the controls of control module 12 himself.) In either case, the controls on control module 12 can all be set before surgery, with the only manipulation of controls required during surgery being switching from one "mode" of operation to another, as explained below.

Handpiece 10 receives irrigation fluid from bottle 28 through irrigation tube 26, which passes through a pinch valve (not visible in FIG. 1) on control module 12. Handpiece 10 is connected to peristaltic aspiration pump 30 on control module 12 through aspiration tube 32, which passes through pump 30 and terminates inside refuse pouch 34. Handpiece 10 is electrically connected to control module 12 by cable 36, control module 12 is electrically connected to foot pedal module 14 by cable 38, and foot pedal module 14 is electrically connected to a power supply by cable 40.

The processing circuitry required to operate the opthalmic surgery system is located in foot pedal module 14 rather than control module 12. Control module 12 is therefore compact and can be located in close proximity to patient 18 without physically interfering with the surgeon's work. Thus, aspiration tube 32 connecting peristaltic pump 30 to handpiece 10 can be relatively short, and consequently peristaltic pump 30 can be relatively small and therefore easily reversible in its direction of operation so that pump 30 can operate in a "reflux" mode (explained below) to eject particles that become lodged in aspiration tube 32 or handpiece 10. As will be seen, control module 12 contains no visual display devices and is therefore relatively simple to use, and, significantly, leaves the surgeon free to concentrate on the surgery itself rather than visually monitoring control module 12.

With reference to FIGS. 2 through 5, control module 12 includes five control knobs but does not contain any visual feedback devices (other than the visual feedback that can be obtained inherently by observing the physical position of the knobs).

Mode selector knob 42 selects one of six modes of operation: "prime," used to prime tubing with irrigation fluid before a handpiece 10 (FIG. 1) is used in surgery; "irrigation only," used to provide irrigation fluid to handpiece 10 with no aspiration; "irrigation/aspiration," used to provide irrigation fluid to handpiece 10 and to provide aspiration; "phaco," used during phaco emulsification; "phaco pulse," used during phaco emulsification if pulsed phaco-power is desired in place of continuous phaco-power; and "ASV™" or "anterior segment vitrector," used in conjunction with a vitrector handpiece (described below).

Aspiration rate knob 44 is used to select a rate of aspiration (anywhere from four milliliters per minute to twenty-two milliliters per minute) at which peristaltic pump 30 is to operate. As is explained below, during the "irrigation/aspiration" and "anterior segment vitrector" modes the aspiration rate varies linearly with depression of foot pedal 20 (FIG. 1), with the maximum rate of aspiration being the rate selected using aspiration rate knob 44. During the "phaco" and "phaco pulse" modes, however, the aspiration rate is always the rate selected using aspiration rate knob 44.

Phaco-power knob 46 is used to select a maximum intensity of power applied to a phaco-emulsification handpiece 10 (FIG. 1) during the "phaco" mode or the "phaco pulse" mode. As is explained below, in these modes of operation the phaco-power varies linearly with depression of foot pedal 20 (FIG. 1), with the maximum phaco-power being the power selected using phaco-power knob 46. Note that the phaco-power selected by phaco-power knob 46 is expressed as a percentage of the total phaco-power available from the unit.

Vacuum control knob 48 is used to select either a high vacuum condition or a low vacuum condition under which aspiration occurs. When the low vacuum condition is selected, vacuum regulator knob 50 is used to select the pressure (anywhere from 25 millimeters of mercury to 125 millimeters of mercury) of the low vacuum. When the high vacuum condition is selected, however, the position of vacuum regulator knob 50 does not affect the pressure of the high vacuum. Vacuum regulator knob 50 sweeps through the entire available range of pressures within one rotation. Because it is possible to discern the pressure that has been selected simply by observing the position of vacuum regulator knob 50, and because the vacuum regulator (described in detail below) is highly accurate (i.e., selected pressure corresponds closely with the actual pressure of the low vacuum), there is no need for a separate visual feedback device (such as a meter or digital readout) to display the pressure.

The vacuum pressure selected by vacuum control knob 48 and vacuum regulator knob 50 is applied to aspiration tube 32 through port 52, to which T-shaped connector 54 is attached. T-shaped connector 54 contains an internal one-way check valve (not shown) that permits air to flow into aspiration tube 32 but prevents fluid from aspiration tube 32 from entering control module 12. As peristaltic pump 30 operates to cause aspiration through aspiration tube 32 at the aspiration rate in milliliters per minute selected by aspiration rate knob 44 (alone or in combination with foot pedal module 14 (FIG. 1), air bleeds into aspiration tube 32 through T-shaped connector 54 at the pressure in millimeters of mercury selected by vacuum control knob 48 and vacuum regulator knob 50, so that the suction through aspiration tube 32 is at the pressure selected by vacuum control knob 48 and vacuum regulator knob 50.

Control module 12 also includes a clamp 56 that forces tube retainer 31 of peristaltic pump 30 to hold tube 32 firmly between the inside of tube retainer 31 and the rotating part of peristaltic pump 30. A pinch valve 58 pinches irrigation tube 26 (FIG. 1) leading from irrigation bottle 28 (FIG. 1) to the handpiece when irrigation is not desired and permits fluid to pass through irrigation tube 26 to handpiece 10 (FIG. 1) when irrigation is desired. Control module 12 also includes an electrical connector 60 for cable leading to phaco handpiece, an electrical connector 62 for a cable leading to a vitrector handpiece, and an electrical connector 64 for a cable leading to foot pedal module 14 (FIG. 1).

Figure 6:
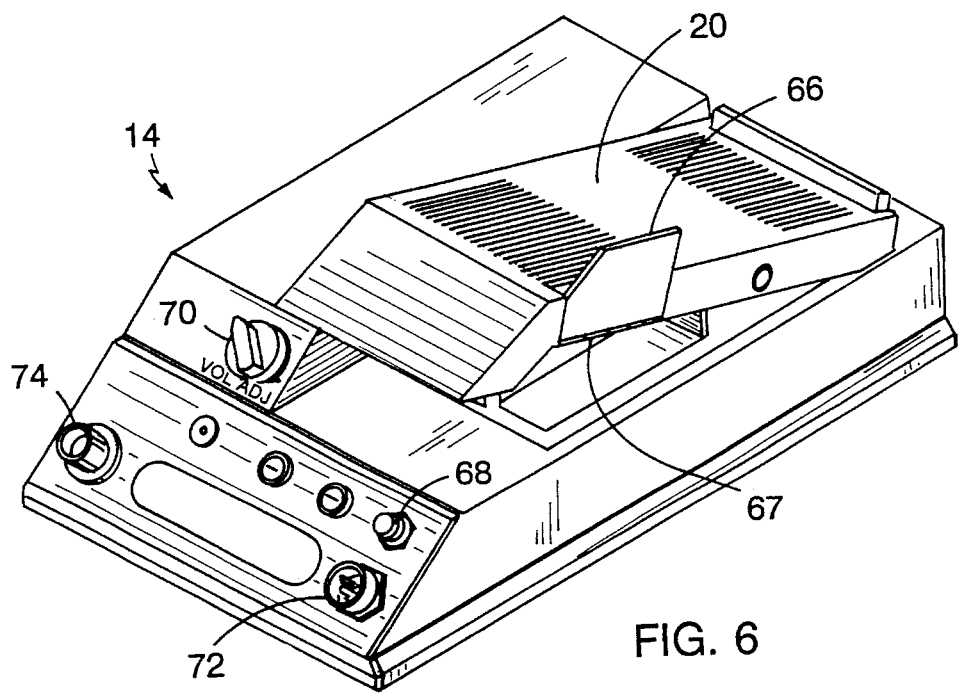
FIG. 6 illustrates the foot pedal module shown in FIG. 1.

With reference to FIG. 6, foot pedal module 14 includes a foot pedal 20, which controls a potentiometer whose resistance varies with movement of the foot pedal, and which is used to manage the operation of the handpieces during surgery in a manner described below. Foot pedal 20 is constructed to have a pair of mechanical detents at two intermediate locations along the travel of the foot pedal from the "full off" position (no depression of the foot pedal) and the "full on" position (full depression of the foot pedal), the detents being arranged such that there is a large amount of travel between the second detent and the "full on" position. Foot pedal module 14 also includes a reflux switch 66, which can be flipped to the side around hinge 67 by sideways pressure of the doctor's foot, to place the opthalmic surgery system in a "reflux" mode, described below, that overrides the foot pedal 20. Reflux switch 66 springs back to its upright position and the "reflux" mode is disabled as soon as the surgeon releases his foot from contact with reflux switch 66. Foot pedal module 14 also includes on/off switch 68, volume adjustment knob 70 for controlling the volume of a beeper located inside foot pedal module 14, an electrical connector 72 for a cable leading to a power supply (such as 120 volts, 60 hertz), and an electrical connector 74 for a cable leading to the control module.

Figure 7:
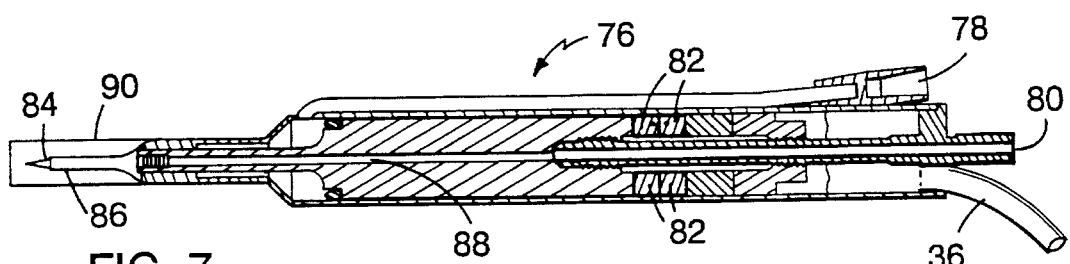
FIG. 7 shows a phaco-emulsification handpiece for use in the system of FIG. 1.
Figure 8:
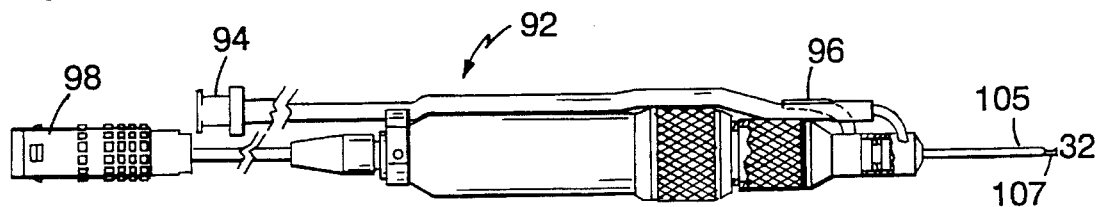
FIG. 8 shows an irrigation and aspiration handpiece for use in the system of FIG. 1.
Figure 9:
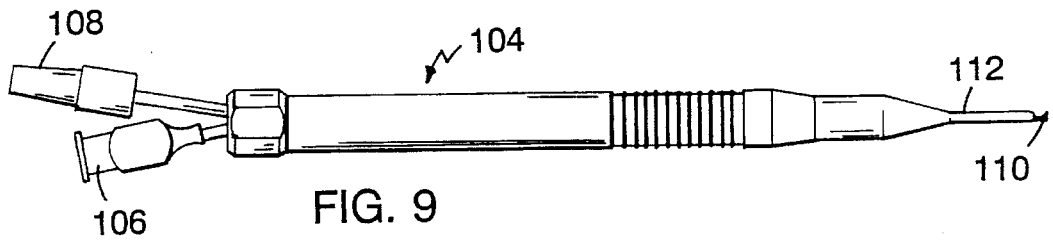
FIG. 9 shows a vitrector handpiece for use in the system of FIG. 1.

FIGS. 7–9 illustrate examples of handpieces 10 that can be used in the eye surgery system.

With reference to FIG. 7, there is shown a phaco-emulsification handpiece 76, used during the "phaco" and "phaco pulse" modes of operation, which includes an irrigation port 78 for receiving irrigation fluid through irrigation tube 26 (FIG. 1), and an aspiration port 80 to which aspiration tube 32 (FIG. 1) is connected. Cable 36 (attached to electrical connector 60 (FIG. 4) on the control module) is connected to piezoelectric elements 82, which vibrate ultrasonically in response to the applied power to cause the phaco-emulsification of the lens in the eye. A hollow needle 84 is attached to the end of the handpiece, and vibration of piezoelectric elements 82 is transmitted to needle 84, which in turn vibrates to emulsify the lens. Irrigation fluid flows out of the handpiece through a silicone irrigation sleeve 86 that is placed over ultrasonic needle 84 and threaded to the distal end of handpiece 76. Aspiration occurs through a tube 88 that runs down the center of handpiece 76 and through needle 84. A silicone cap 90 is slid onto the distal end of handpiece 76 over irrigation sleeve 86 during the "prime" mode of operation, as explained below.

With reference to FIG. 8, there is shown a vitrector handpiece 92, used during the "anterior segment vitrector" mode of operation, which includes an irrigation port 94 for receiving irrigation fluid through irrigation tube 26 (FIG. 1), and an aspiration port 96 to which aspiration tube 32 (FIG. 1) is connected. Electrical connector 36 is connected to an electrical receptacle 98. Electric power is applied to a cutter that reciprocates, rotates, or slices in the vicinity of an opening in the end of a hollow tube 102 that runs down the center of the handpiece. Irrigation fluid flows out of the end of an irrigation sleeve 100 that surrounds tube 102 except at the tip, and aspiration occurs from the opening in the distal end of hollow tube 102 through the center of tube 102 to aspiration port 96.

With reference to FIG. 9, there is shown an irrigation/aspiration handpiece 104, used during the "irrigation/aspiration" mode of operation, which includes an irrigation port 106 for receiving irrigation fluid through irrigation tube 26 (FIG. 1), and an aspiration port 108 to which aspiration tube 32 (FIG. 1) is connected. Aspiration occurs through the center of a tube 110 that runs down the center of handpiece 104, and irrigation fluid flows out of the end of an irrigation sleeve 112 that surrounds tube 110 except at the tip.

Figure 10:
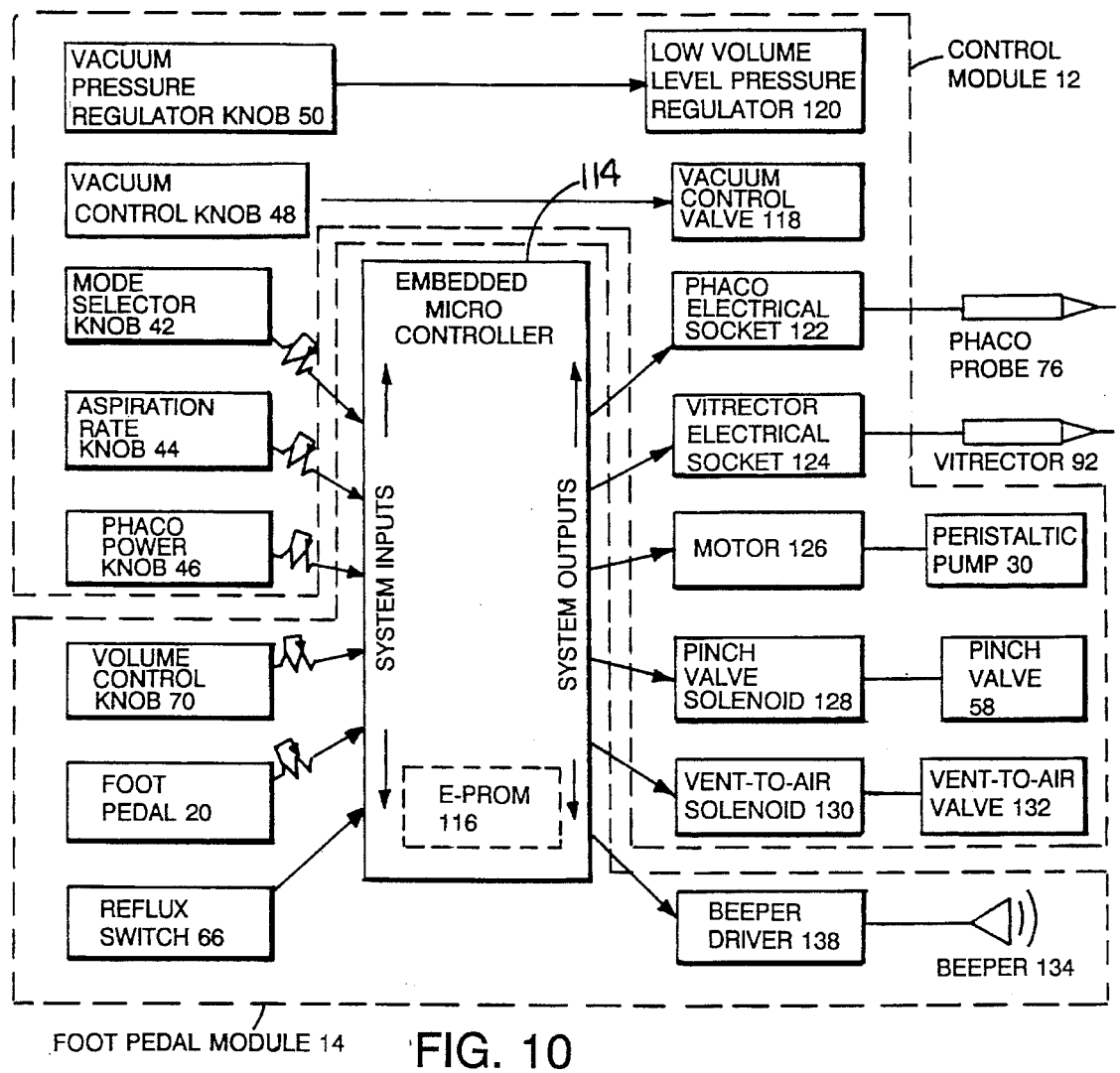
FIG. 10 is a block diagram of the circuitry of the ophthalmic surgery system of FIG. 1.

With reference to FIG. 10 there is shown a block diagram of the circuitry of the ophthalmic surgery system of FIG. 1. The signal processing circuitry of the system is contained in an embedded microcontroller 114 contained within foot pedal module 14, the operation of microcontroller 114 being controlled by e-prom 116. Mode selector knob 42, aspiration rate knob 44, phaco-power knob 46, volume control knob 70, and foot pedal 20 all simply control resistive potentiometers to which microcontroller 114 is directly connected. (The potentiometers controlled by knobs 42, 44 and 46 are connected to microcontroller 114 via cable 38, while the volume control and foot pedal potentiometers are internal to foot pedal module 14.) The only other input to microcontroller 114 is from reflux switch 66, which is not a potentiometer but a switch. Microcontroller 114 measures the voltage through each potentiometer as a raw input and interprets these raw inputs as programmed by e-prom 116 either to represent a variable quantity (e.g., aspiration rate, phaco-power, beeper volume) or one of a set of discrete modes or events (e.g., the modes selected by mode selector knob 42 or the events that occur as foot pedal 20 passes through certain points).

Microcontroller 114 interprets the voltages across the potentiometers and responds by sending appropriate electrical signals through cable 38 to phaco electrical socket 122 (for phaco handpiece 76), vitrector electrical socket 124 (for vitrector 92), pump motor (for peristaltic pump 30), pinch valve solenoid 128 (for pinch valve 58), and vent-to-air solenoid 130 (for vent-to-air valve 132, the function of which is described below), all of which are connected as system outputs of embedded microcontroller 114, and by sending appropriate electrical signals to beeper driver 138 in the foot pedal module 14.

Control module 12 also includes a vacuum control valve 118 mechanically controlled by vacuum control knob 48 and a low vacuum level pressure regulator 120 mechanically controlled by vacuum pressure regulator knob 50.

It can be seen that control module 12 simply contains a set of potentiometers, electrical sockets, solenoids, valves, etc., but contains no signal processing circuitry. Because the circuitry is within foot pedal module 14 rather than control module 12, control module 12 is relatively compact and therefore can be located close to the patient without physically interfering with the surgeon's work.

Figure 11:
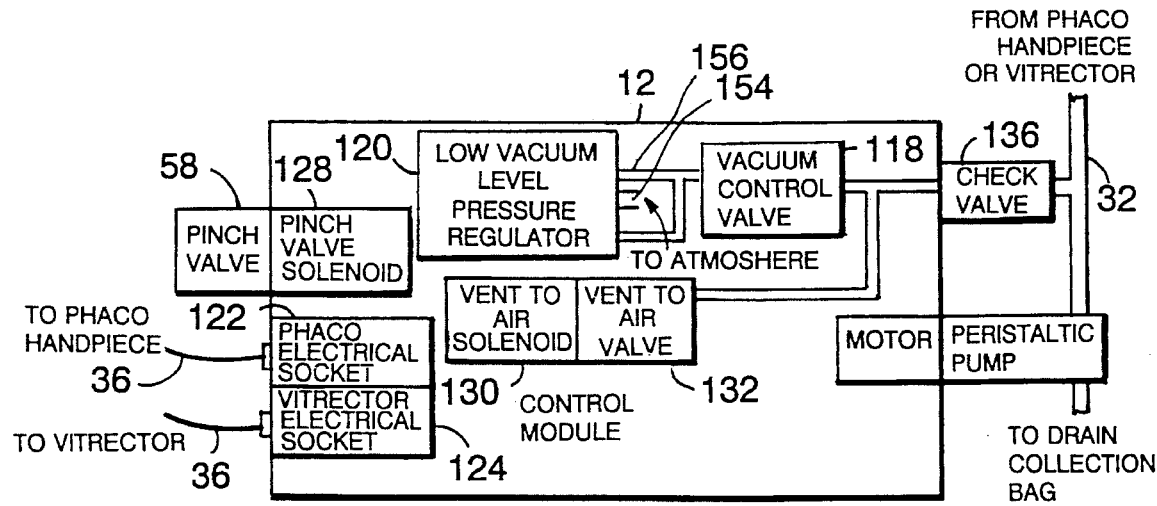
FIG. 11 is a functional block diagram of the control module of FIG. 2.

With reference to FIG. 11, there is shown a functional block diagram of control module 12, showing the functional interrelationship of various items located within the dashed line in FIG. 10 corresponding to control module 12. Note that aspiration tube 32 is connected to control module 14 through a one-way check valve 136 that permits air to flow into aspiration tube 32 but prevents fluid from aspiration tube 32 from entering the internal tubing of control module 12. Vacuum control valve 118 either isolates low vacuum level pressure regulator 120 from the remainder of the internal tubing (when "high" vacuum level is selected via vacuum control knob 48 shown in FIG. 2) or connects low vacuum level pressure regulator 120 with the remainder of the internal tubing (when "low" vacuum level is selected). Low vacuum level pressure regulator 120, controlled by pressure regulator knob 50 (FIG. 2), permits air to enter the internal tubing until the desired low vacuum pressure is achieved. Low vacuum level pressure regulator 120, which has two connections to the internal tubing of the control module has one connection to atmosphere, is described in detail below in connection with FIG. 12. Vent-to-air valve 132, when activated by vent-to-air solenoid 130, permits air to enter the internal tubing at atmospheric pressure.

With reference to FIG. 12, precision vacuum pressure regulator 120 includes a housing 140 that is divided into an upper chamber 142, an annular lower chamber 144, and a central lower chamber 146. Membrane 148 separates upper chamber 142 from lower chambers 144 and 146. Annular lower chamber 144 is exposed to atmospheric pressure through outlet 154 while central lower chamber 146 and upper chamber 142 are connected to the internal tubing of the control module through outlets 156 and 158 respectively, the operation of the peristaltic pump causing suction through this internal tubing. When vacuum pressure regulator knob 50 is rotated clockwise springs 150 and 152 are compressed downward, and when vacuum pressure regulator knob 50 is rotated counter-clockwise the downward compression of springs 150 and 152 is reduced. At any given rotational position of vacuum pressure regulator knob 50 air will flow from annular lower chamber 144 to central lower chamber 146 through small annular gap 160 in wall 161 between these two chambers to maintain an equilibrium pressure in the internal tubing of the control module and hence in upper chamber 142 that is sufficient for the air in upper chamber 142 to force membrane 148 downward to cause annular gap 160 to achieve an equilibrium size. The equilibrium pressure in the internal tubing of the control module is controlled with a high degree of precision by the rotation of vacuum pressure regulator knob 50, which sweeps through the entire range of available equilibrium pressures within a single rotation.

Operation

With reference to FIG. 13, the "prime" mode of operation is used to flush air bubbles from the tubes leading to and from any of handpieces 10 (FIG. 1) before the handpiece is used during surgery. First (step 200), a cap 90 (FIG. 7) is slid onto the handpiece. Then (step 202), mode selector switch 42 (FIG. 2) is set to "prime." When the mode selector switch is set to "prime," the corresponding potentiometer voltage is sensed by microcontroller 114 (FIG. 10) in foot pedal module 14, which responds by signalling pinch valve solenoid 128 (FIG. 10) to open pinch valve 58 (or keep it open), signalling pump motor 126 to run counter-clockwise at full speed regardless of the setting of the "aspiration rate" knob (or to keep running counter-clockwise at full speed, etc.), deactivating phaco electrical socket 122 and vitrector electrical socket 124, and signalling vent-to-air solenoid to close vent-to-air valve 132 (step 204). Irrigation fluid flows through the handpiece into cap 90 (FIG. 7) and is aspirated out of the handpiece through aspiration tubing 32 (FIG. 1). When the air bubbles are observed to have disappeared from the tubes leading to and from the handpiece, handpiece 10 is ready for use (step 206), mode selector switch 50 (FIG. 2) is switched from "prime," and the cap can be removed from the handpiece. Note that the entire foot pedal module, including both foot pedal 20 (FIG. 6) and the reflux switch 67 (FIG. 6), are disabled during the "prime" mode.

With reference to FIG. 14, the "irrigation only" mode of operation may be used while the capsule of the eye is being cut with a handpiece. First mode selector switch 50 (FIG. 2) is set at "irrigation only" while foot pedal 20 (FIG. 6) is in its full off position (no depression) (step 208). When mode selector switch 50 is set at "irrigation only" with foot pedal 20 in the full off position microcontroller 114 signals pinch valve solenoid 128 to close pinch valve 58, turns pump motor 126, deactivates phaco electrical socket 122 and vitrector electrical socket 124, and signals pinch valve solenoid 128 to close vent-to-air valve 132 (step 210). Then foot pedal 20 is depressed past one-half the distance to the first of two detents (step 212), and microcontroller 114 responds by signalling pinch valve 128 to open pinch valve 58, causing irrigation fluid to flow through handpiece 10 (step 214). When foot pedal 20 is released past one-half the distance from full off to the first detent (step 216), microcontroller 144 signals pinch valve solenoid 128 to close pinch valve 58 (step 218). Note that the entire foot pedal module 14, including both foot pedal 20 and reflux switch 67, are disabled during the "irrigation only" mode.

Figure 15A:
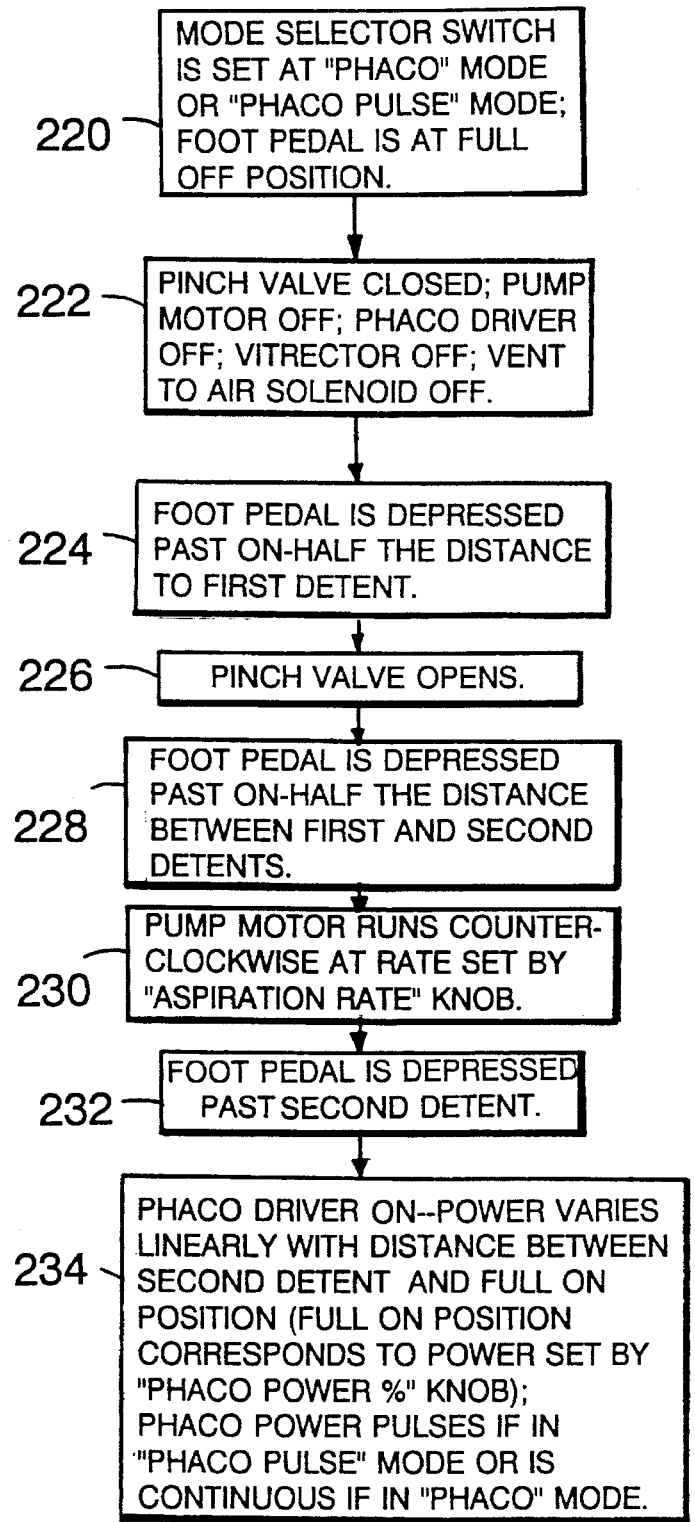
FIG. 15 is a flowchart illustrating the operation of the ophthalmic surgery system of FIG. 1 during the "phaco" mode or the "phaco pulse" mode.
Figure 15B:
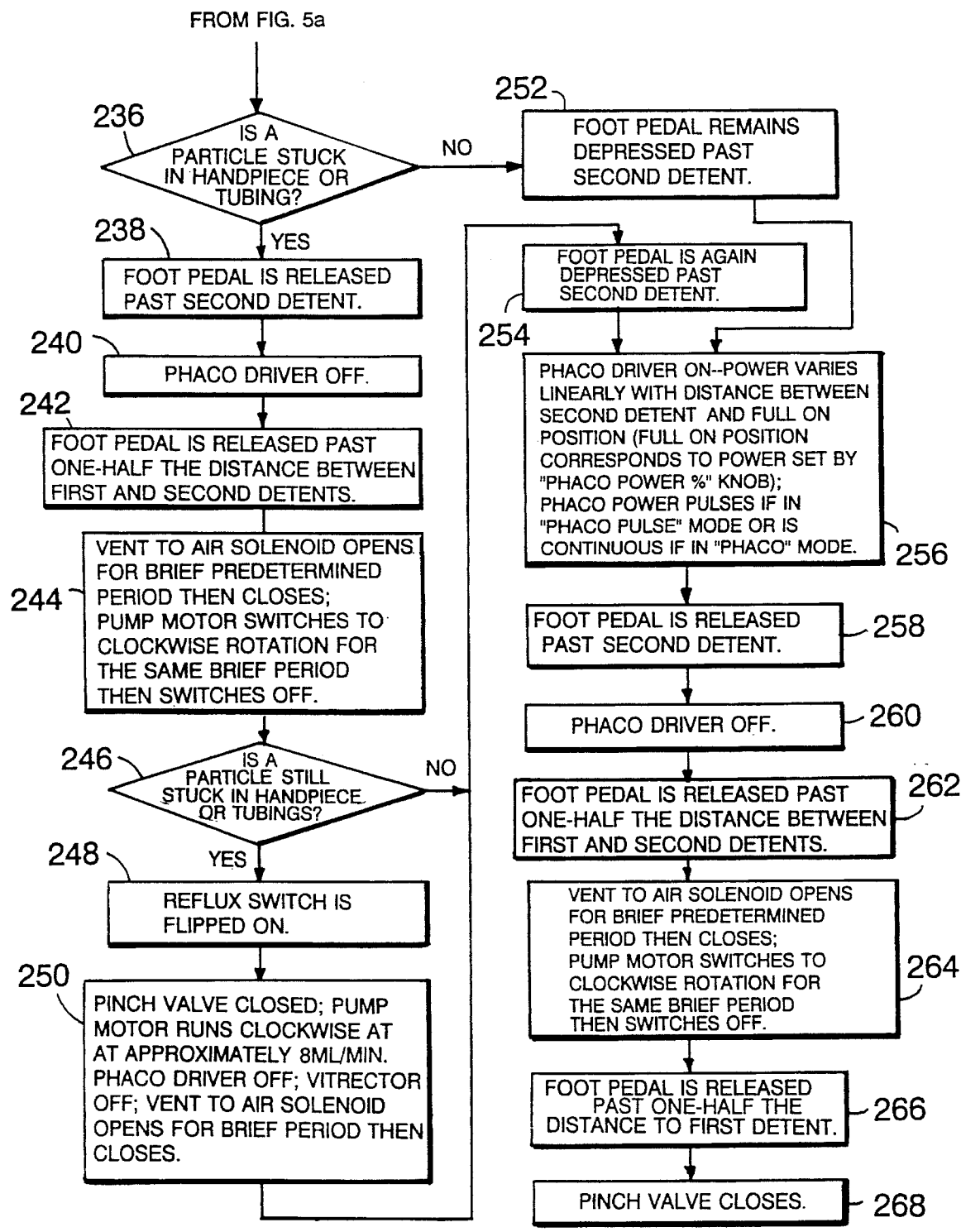

With reference to FIG. 15, the "phaco" and "phaco pulse" modes of operation are used during phaco-emulsification of the patient's lens using a phaco-emulsification handpiece. First (step 220), mode selector switch 50 is set at "phaco" or "phaco pulse" while foot pedal 20 is in its full off position. When mode selector switch 50 is set at "phaco" or "phaco pulse" with foot pedal 20 in the full off position, microcontroller 144 signals pinch valve solenoid 128 to close pinch valve 58, turns pump motor 126 off, deactivates phaco electrical socket 122 and vitrector electrical socket 124, and signals vent-to-air solenoid 130 to close vent-to-air valve 132 (step 222). Then foot pedal 20 is depressed past one-half the distance to the first detent (step 224), and microcontroller 114 responds by signalling pinch valve solenoid 128 to open pinch valve 58, causing irrigation fluid to flow through the handpiece (step 226). When foot pedal 20 is depressed past one-half the distance between the first and second detents (step 228), microcontroller 114 signals pump motor 126 to run counter-clockwise at a rate set by "aspiration rate" knob 44 (step 230). When foot pedal 20 is depressed past the second detent (step 232), microcontroller 114 activates phaco electrical socket 122, the power varying linearly with the position of foot pedal 20 between the second detent and the full on position (complete depression of foot pedal 20), the full on position corresponding to the power set by "phaco-power" knob 46 (step 234). The phaco-power pulses ten times per second if the system is in the "phaco pulse" mode and is continuous if the system is in the "phaco" mode. Every thirty seconds microcontroller 144 signals beeper driver 138 to cause beeper 134 in foot pedal module 14 to beep, once after the first thirty seconds, twice after the first minute, etc., as an indication of the extent of time for which phaco-power has been applied, thereby eliminating any need for the surgeon to observe a visual feedback display on the control module or elsewhere (which a typical surgeon might not do at all) to find out how long the phaco-power has been applied.

If at any point during phaco-emulsification a particle becomes lodged in handpiece 10 or aspiration tubing 32 (step 236), foot pedal 20 is released past the second detent (step 238) and microcontroller 114 responds by deactivating phaco electrical socket 122 (step 240), and foot pedal 20 is released past one-half the distance between the first and second detents (step 242) and microcontroller 114 responds by signalling vent-to-air solenoid 130 to open vent-to-air valve 132 for a brief predetermined time then close and switches pump motor 126 to clockwise rotation for the same brief period then switch off (step 244). This "mini-reflux" is usually adequate to release the particle. If the particle is still lodged in handpiece 10 or aspiration tubing 32 (step 246), however, the surgeon flips reflux switch 67 on foot pedal module 14 (step 248), and microcontroller 114 responds by signalling pinch valve solenoid 128 to close pinch valve 58, signalling pump motor 126 to run clockwise at approximately 8 milliliters per minute, signalling vent-to-air solenoid 130 to open vent-to-air valve 132 for a brief period then close, and deactivating phaco electrical socket 122 and vitrector electrical socket 124 (step 250). Reflux switch 67 overrides foot pedal 20 regardless of the extent to which foot pedal 20 is depressed, and provides a convenient way for the surgeon to enter a "reflux" mode of operation without requiring the surgeon to manipulate the controls on control module 12. Microcontroller 114 signals beeper driver 138 to cause beeper 134 on foot pedal module 14 to beep repeatedly as long as reflux switch 67 is flipped, to indicate to the surgeon that the system is in reflux. Thus, the system does not require the surgeon to observe a visual display (which a typical surgeon might not do at all) to discover that the system is in reflux.

After the particle is released, foot pedal 20 is again depressed past the second-detent if necessary until the lens is sufficiently emulsified (steps 252, 254, and 256). Then foot pedal 20 is released past the second detent (step 258), and microcontroller 114 responds by deactivating phaco electrical socket 122 (step 260). When foot pedal 20 is released past one-half the distance between the first and second detents (step 262), microcontroller 114 signals vent-to-air solenoid 130 to open vent-to-air valve 132 for a brief period then closes and switches pump motor 126 to clockwise rotation for the same brief period then switches pump motor 126 off (the "mini-reflux") (step 264). When foot pedal 20 is released past one-half the distance from full off to the first detent (step 266), microcontroller 114 signals pinch valve solenoid 128 to close pinch valve 58 (step 268).

Figure 16:
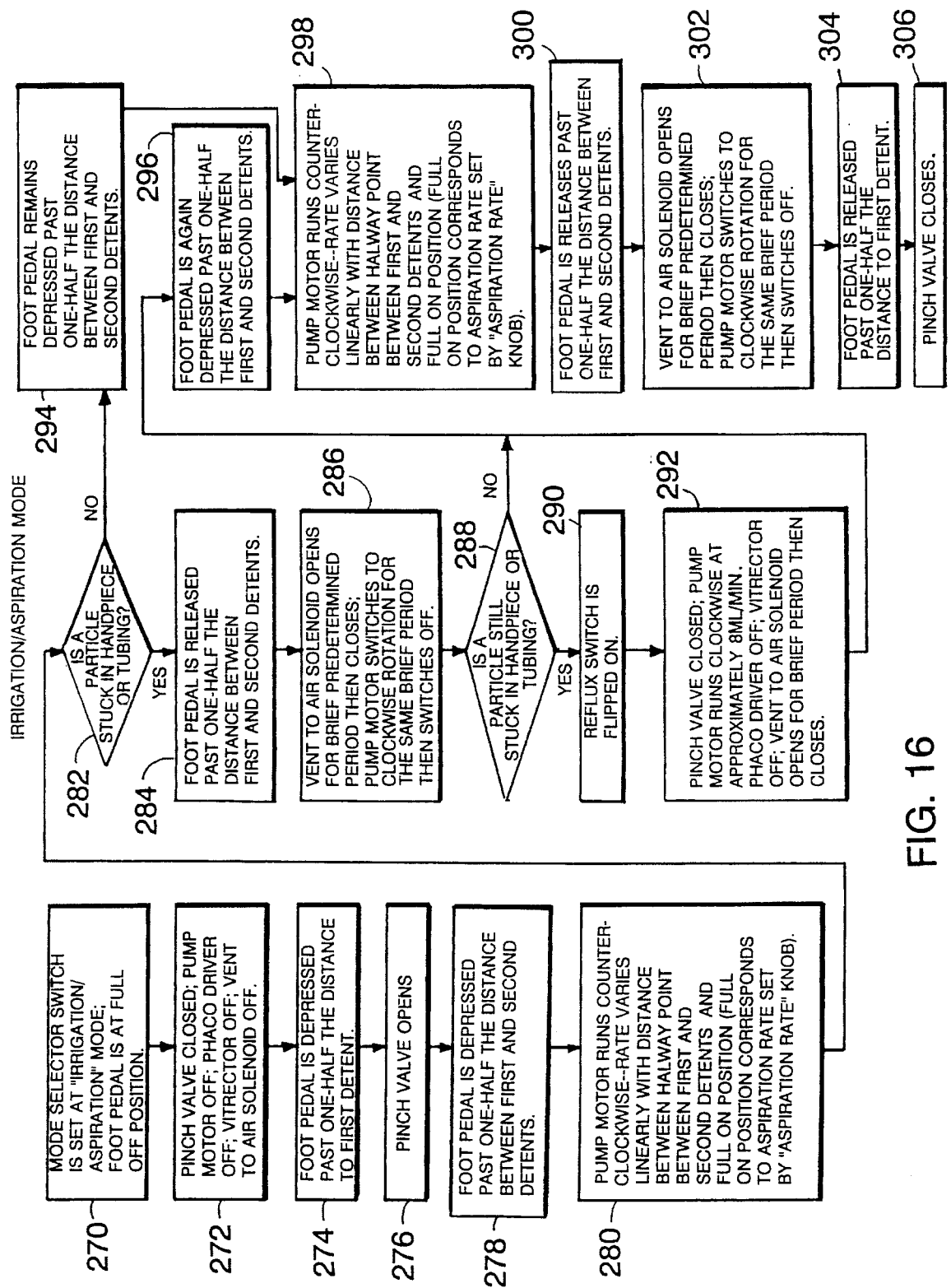
FIG. 16 is a flowchart illustrating the operation of the ophthalmic surgery system of FIG. 1 during the "irrigation/aspiration" mode.

With reference to FIG. 16, the "irrigation/aspiration" mode of operation is used in conjunction with the irrigator/aspirator shown in FIG. 9 after phaco-emulsification of the patient's lens to remove the remaining lens particles from the capsule of the eye. First, (step 270) mode selector switch 50 is set at "irrigator/aspirator" while foot pedal 20 is in its full off position. When mode selector switch 50 is set at "irrigator/aspirator" with foot pedal 20 in the full off position, microcontroller 114 signals pinch valve solenoid 128 to close pinch valve 58, switches pump motor 126 off, deactivates phaco electrical socket 122 vitrector electrical socket 124, and signals vent-to-air solenoid 130 to close vent-to-air valve 132 (step 272). Then foot pedal 20 is depressed past one-half the distance to the first detent (step 274), and microcontroller 114 responds by signalling pinch valve solenoid 128 to open pinch valve 58, causing irrigation fluid to flow through handpiece 10 (step 276). When foot pedal 20 is depressed past one-half the distance between the first and second detents (step 278), microcontroller 114 signals pump motor 126 to run counter-clockwise (step 280). The rate at which pump motor 126 runs varies linearly with the position of foot pedal 20 between two endpoints. One of the endpoints is the halfway point between the first and second detents and the other endpoint is the "full on" position (complete depression of foot pedal 20). The "full on" position corresponds to the aspiration rate set by "aspiration rate" knob 44. Microcontroller 114 signals beeper driver 138 to cause beeper 134 on foot pedal module 14 to emit a tone that increases in frequency as the rate of aspiration increases and decreases in frequency as the rate of aspiration decreases, thereby providing an indication to the surgeon of the rate of aspiration.

If at any point during irrigation/aspiration a particle becomes lodged in handpiece 10 or aspiration tubing 32 (step 282), foot pedal 20 is released past one-half the distance between the first and second detents (step 284), and microcontroller 114 responds by signalling vent-to-air solenoid 130 to open vent-to-air valve 132 for a brief predetermined time then close and switches pump motor 126 to clockwise rotation for the same brief period then switch pump motor 126 off (the same "mini-reflux" that is available in "phaco" and "phaco pulse" modes) (step 286). If the particle is still lodged in handpiece 10 or aspiration tubing 32 (step 288), the surgeon flips reflux switch 67 on foot pedal module 14 (step 290), and microcontroller 114 responds by signalling pinch valve solenoid 128 to close pinch valve 58, signalling pump motor 126 to run clockwise at approximately 8 milliliters per minute, signalling vent-to-air solenoid 130 to open vent-to-air valve 132 for a brief period then close, and deactivating with phaco electrical socket 122 and vitrector electrical socket 124 (the same reflux that is available in "phaco" and "phaco pulse" modes) (step 292).

After the particle is released, foot pedal 20 is again depressed if necessary past one-half the distance between the first and second detents to continue aspiration (steps 294, 296, and 298). When aspiration is complete, foot pedal 20 is released past one-half the distance between the first and second detents (step 300), and microcontroller 114 responds by signalling vent-to-air solenoid 130 to open vent-to-air valve 132 for a brief period then close and switching pump motor 126 to clockwise rotation for the same brief period then switch off (the "mini-reflux") (step 302). When foot pedal 20 is released past one-half the distance from full off to the first detent (step 304), microcontroller 114 signals pinch valve solenoid 128 to close pinch valve 58 (step 306).

Figure 17:
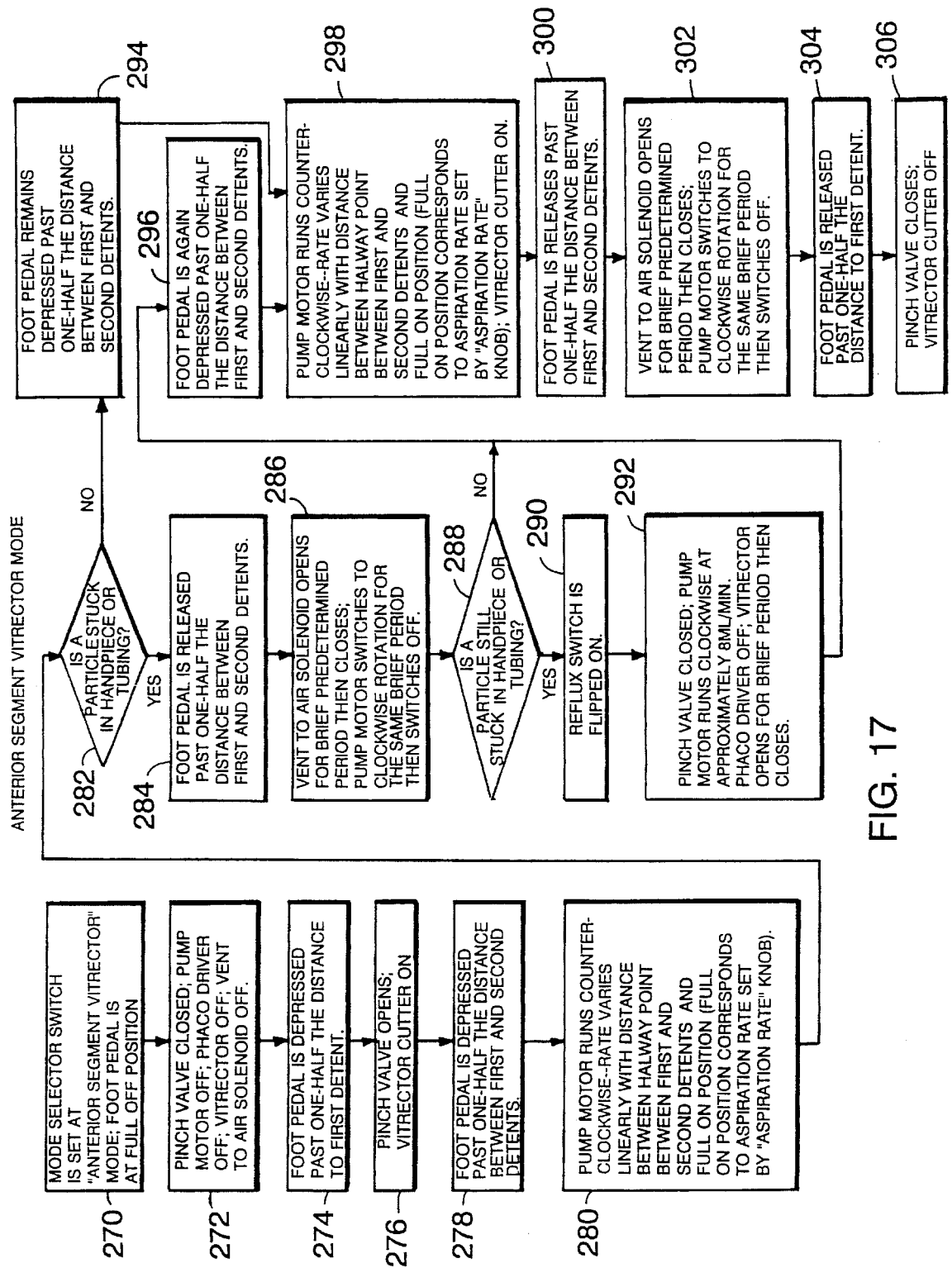
FIG. 17 is a flowchart illustrating the operation of the ophthalmic surgery system of FIG. 1 during the "anterior segment vitrector" ("ASV™") mode.

With reference to FIG. 17, the "anterior segment vitrector" mode of operation is used in conjunction with vitrector 92 shown in FIG. 8 in the event that the surgeon accidentally punctures the lens capsule causing vitreous fluid to enter the capsule. Vitrector 92 is used to slice off the vitreous fluid that has entered the capsule. Once this fluid is sliced off and a pressure balance is achieved the fluid stops entering the capsule.

The "anterior segment vitrector" mode of operation functions in exactly the same manner as the "irrigation/aspiration" mode of operation in every respect, except that in the "anterior segment vitrector" mode of operation microcontroller 114 activates vitrector electrical socket 124 (steps 276 and 298) when foot pedal 20 is depressed past one-half the distance between "full off" and the first detent (steps 274 and 296) and deactivates vitrector electrical socket 124 (step 306) when foot pedal 20 is released past one-half the distance between "full off" and the first detent (step 304).

It will be apparent from the above that all of the controls on control module 12 can be set at their appropriate settings before surgery commences, and that the only manipulation of any of the control knobs on control module 12 that is required during surgery is manipulation of "mode selector" knob 50, which can easily be performed by a scrub nurse at the instruction of the surgeon. The surgeon need never look at any visual display device, and is therefore free to concentrate on the surgery itself.

There has been described novel and improved apparatus and techniques for controlling the operation of handpieces during ophthalmic surgery. It is evident that those skilled in the art may now make numerous uses and modifications of and departures from the specific embodiment described herein without departing from the inventive concept. Consequently, the invention is to be construed as embracing each and every novel feature and novel combination of features present in or possessed by the apparatus and technique herein disclosed and limited solely by the spirit and scope of the appended claims.

What is claimed is:

1. A system for operating on a patient's eye, comprising a handpiece constructed for insertion by a user into said eye, a control module comprising at least one control arranged to be manipulated by a user to control a setting of at least one parameter of operation of said handpiece, said control being arranged to generate a first signal that indicates the setting of said at least one parameter, and a foot pedal module comprising a foot pedal arranged to generate a second signal, in response to actuation of said foot pedal by the user, for controlling operation of said handpiece in accordance with said parameter set by said control in said control module, said foot pedal module further comprising circuitry connected to said control in said control module, to said foot pedal, and to said handpiece, said circuitry being located within said foot pedal module and being arranged to process said first signal and said second signal to generate an output signal to control the operation of said handpiece, said output signal being based on the setting of said at least one parameter and the actuation of said foot pedal, wherein said circuitry located within said foot pedal module comprises substantially all of the circuitry of said system and performs substantially all processing of signals in said system.

2. A system in accordance with claim 1 wherein said handpiece comprises an irrigation and aspiration device.

3. A system in accordance with claim 2, wherein said parameter of operation of said handpiece set by said control in said control module comprises a maximum aspiration rate, depression of said foot pedal first causes irrigation to begin and then causes aspiration to begin, the rate of aspiration varying linearly with the amount of depression of said foot pedal up to said maximum aspiration rate, and release of said foot pedal first causes aspiration to end and then causes irrigation to end.

4. A system in accordance with claim 1 wherein said handpiece comprises a phaco-emulsification device.

5. A system in accordance with claim 4, wherein said at least one parameter of operation of said handpiece set by said control in said control module comprises an aspiration rate and a maximum intensity of phaco-power, depression of said foot pedal first causes irrigation to begin, then causes aspiration to begin at said aspiration rate set by said control in said control module, and then causes phaco-power to be applied to said handpiece, the intensity of said phaco-power varying linearly with the amount of depression of said foot pedal up to said maximum intensity of phaco-power, and release of said foot pedal first causes application of phaco-power to end, then causes aspiration to end, and then causes irrigation to end.

6. A system in accordance with claim 1 wherein said handpiece comprises a vitrector.

7. A system in accordance with claim 6, wherein said at least one parameter of operation of said handpiece set by said control in said control module comprises a maximum aspiration rate, depression of said foot pedal first causes irrigation to begin and cutting to begin and then causes aspiration to begin, the rate of aspiration varying linearly with the amount of depression of said foot pedal up to said maximum aspiration rate, and release of said foot pedal first causes aspiration to end and then causes cutting and irrigation to end.

8. A system for operating on a patient's eye, comprising a handpiece constructed for insertion by a user into said eye, a control module comprising a plurality of controls each of which comprises a user-graspable portion arranged to be manipulated manually to multiple positions by the user, said control module being coupled with said handpiece in a manner such that manual manipulation of each of said controls results in variation of a respective parameter of operation of said handpiece, wherein visual feedback from said system with respect to all parameters of operation of said handpiece is provided exclusively by observation of the displacement of said user-graspable portions of said plurality of controls relative to fixed markings on said control module, and a foot pedal module electrically connected to said control module and comprising a foot pedal with which operation of said handpiece is controllable in accordance with said parameters set by said controls in said control module.

9. A system in accordance with claim 8 wherein said plurality of parameters of operation comprises an aspiration rate.

10. A system in accordance with claim 8, wherein said handpiece comprises a phaco-emulsification device, and said plurality of parameters of operation comprises an intensity of phaco-power.

11. A system for operating on a patient's eye, comprising a handpiece constructed for insertion into said eye, a pump, connected to said handpiece by tubing, said pump being arranged to produce aspiration through said tubing, and a control module connected to said tubing and comprising a vacuum regulator, said vacuum regulator comprising a user-graspable portion arranged for selecting any one of a plurality of aspiration pressures within said tubing, visual feedback of aspiration pressure being provided solely through observation of the displacement of said user-graspable portion of said vacuum regulator relative to fixed markings on said control module.

12. A system in accordance with claim 11 wherein said vacuum regulator comprises a rotatable knob that sweeps from a minimum pressure to a maximum pressure within one full rotation of said rotatable knob.

13. A system in accordance with claim 11 wherein said control module further comprises a vacuum control switch arranged to switch between a high vacuum mode in which said vacuum regulator is disabled and a low vacuum mode in which said vacuum regulator is operable.

14. A system for operating on a patient's eye, comprising a handpiece constructed for insertion by a user into said eye, a pump, connected to said handpiece by tubing, said pump being arranged to operate in a first direction to produce aspiration through said handpiece and said tubing, a foot pedal module comprising a foot pedal, said foot pedal module being coupled with said handpiece in a manner such that manipulation of said foot pedal controls operation of said handpiece, and a reflux switch coupled with said foot pedal module in a manner such that manipulation of said reflux switch from a first position to a second position overrides operation of said foot pedal regardless of the position of said foot pedal by causing said pump to operate indefinitely and continuously in a second direction opposite to said first direction, as long as said reflux switch is in said second position, to force fluid through said tubing in a direction opposite to the direction in which fluid flows through said tubing during aspiration.

15. A system in accordance with claim 14 wherein said reflux switch is located on said foot pedal.

16. A system in accordance with claim 14, wherein said handpiece comprises an irrigation and aspiration device, depression of said foot pedal first causes irrigation to begin and then causes aspiration to begin, and release of said foot pedal first causes aspiration to end and then causes irrigation to end.

17. A system in accordance with claim 14, wherein said handpiece comprises a phaco-emulsification device, depression of said foot pedal first causes irrigation to begin, then causes aspiration to begin, and then causes phaco-power to be applied to said handpiece,, and release of said foot pedal first causes application of phaco-power to end, then causes aspiration to end, and then causes irrigation to end.

18. A system in accordance with claim 14, wherein said handpiece comprises a vitrector, depression of said foot pedal first causes irrigation to begin and cutting to begin and then causes aspiration to begin, and release of said foot pedal first causes aspiration to end and then causes cutting and irrigation to end.

19. A system in accordance with claim 14, further comprising an auditory indicator arranged to produce an audible signal while said pump is operating in said second direction.

20. A system for operating on a patient's eye, comprising a handpiece constructed for insertion by a user into said eye, a foot pedal module comprising a foot pedal, said foot pedal module being coupled with said handpiece in a manner such that manipulation of said foot pedal controls application of electrical power to said handpiece, and an auditory indicator coupled with said foot pedal module in a manner such that said auditory indicator is arranged to produce an audible timing signal that is introduced at the end of a predetermined time interval after initiation of application of said electrical power to said handpiece.

\* \* \* \* \*